United States Patent [19]

Boris

[11] 3,934,015

[45] Jan. 20, 1976

[54] ORAL MALE ANTIFERTILITY METHOD AND COMPOSITIONS

[75] Inventor: Alfred Boris, Parsippany-Troy Hills, N.J.

[73] Assignee: Hoffmann-La Roche Inc., Nutley, N.J.

[22] Filed: Nov. 5, 1970

[21] Appl. No.: 87,328

[52] U.S. Cl. .......... 424/267; 424/248; 424/DIG. 12
[51] Int. Cl.$^2$........................................ A61K 31/445
[58] Field of Search............................ 424/248, 267

[56] References Cited
FOREIGN PATENTS OR APPLICATIONS

| | | |
|---|---|---|
| 763,406 | 12/1956 | United Kingdom................. 424/248 |
| 1,123,656 | 8/1968 | United Kingdom................. 424/248 |
| 1,142,724 | 2/1969 | United Kingdom................. 424/248 |

OTHER PUBLICATIONS

Lynch et al., Journal of Organic Chemistry, 10/1966, Vol. 31, pp. 3337–3342.

Primary Examiner—Norman A. Drezin
Attorney, Agent, or Firm—Samuel L. Welt; Jon S. Saxe; George M. Gould

[57] ABSTRACT

A class of substituted 2-cycloalkylaminoalkylphenols, preferably D,L-6-(N-α-pipecolinomethyl)-5-hydroxyindane, enantiomers thereof and acid addition salts thereof have been found to exhibit oral antifertility activity in male aves and mammals. These compounds may therefore be utilized to induce temporary or non-reversible sterility in treated subjects.

8 Claims, No Drawings

ORAL MALE ANTIFERTILITY METHOD AND COMPOSITIONS

BACKGROUND OF THE INVENTION

D,L-6-(N-α-pipecolinomethyl)-5-hydroxyindane and its acid addition salts have been described in British Pat. No. 763,406. These compounds have been indicated to be useful i.v. as oxytoxics and were observed in humans to promote a rhythymic contraction of the uterus without a rise in tonus. The utility of these compounds was limited to treatment of pregnant mammalian females as a means of inducing labor.

Additional disclosures relating to the use of D,L-6-(N-α-pipecolinomethyl)-5-hydroxyindane, the levorotary and dextrorotary enantiomers thereof and several related substituted 2-cycloalkylaminoalkylphenols as oxytoxic agents is to be found in the paper by Cohen et al., Brit. J. Pharmacol. 12, 194 (1957).

BRIEF DESCRIPTION OF THE INVENTION

The present invention relates to a novel method for chemically inducing either temporary or non-reversible sterility in avian or mammalian males. The basis of the present invention resides in the discovery that compounds of the formula

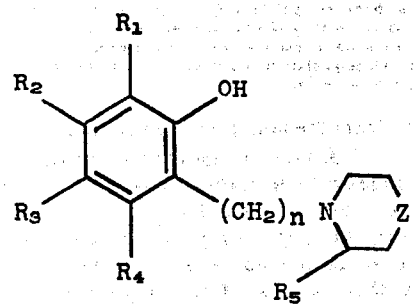

wherein
$Z$ is —O— or —CH$_2$—, $R_1$ independently is hydrogen, N-piperidino-lower alkyl and N-α-pipecolino lower alkyl,
$R_2$, $R_3$ and $R_4$ independently are hydrogen or lower alkyl,
$R_1$, $R_2$, $R_3$ and $R_4$ taken together as adjacent pairs are lower alkyl having from 3 to 5 carbon atoms, $R_5$ is hydrogen or lower alkyl and $n$ is 1 or 2
and the enantiomers and acid addition salts thereof have substantial antifertility activity when administered to male aves and mammals. As indicated above, these compounds have previously been utilized solely in the treatment of females as an oxytoxic.

The method of the present invention would therefore be utilized, for example, in human males to induce permanent sterility without the necessity of surgical intervention, e.g., in lieu of a vasectomy. Additionally, the method of the present invention could be utilized in the biological control of pests, such as avian pests, particularly starlings and pigeons or rodent pests, particularly rats. For example, a single feeding could sterilize male pests thus preventing or reducing fertile mating. Such infertile mating would also induce pseudopregnancy in some female pests which would preclude possible fertile matings with unexposed males for the duration of the pseudo-pregnant period. In this manner the pest population in a locus could be significantly decreased.

Examples of suitable compounds of formula I for use in the practice of this invention include the following:
6-(N-α-pipecolinomethyl)-5-hydroxyindane
5-(1-piperidylmethyl)-4-indanol
4,6-bis(1-piperidylmethyl)-5-indanol
2-N-piperidinomethyl-4,5-dimethylphenol
2-(N-α-pipecolinomethyl)-4,5-dimethylphenol
4,6-bis[(2-methylpiperidino)methyl]-5-indanol
2-(3'-methyl-4-morpholinomethyl)-4,5-dimethylphenol
2-(β-N-piperidinoethyl)-4,5-dimethylphenol
6-(3'-methyl-4'-morpholinomethyl)-5-hydroxyindane As used herein the term acid addition salts is meant to include salts of organic and inorganic acids such as hydrochloric acid, hydrobromic acid, sulfonic acid, p-toluenesulfonic, phosphoric acid, nitric acid, tartaric acid, citric acid, camphorsulfonic acid, ethanesulfonic acid, ascorbic acid, salicylic acid, maleic acid and the like. A particularly preferred inorganic salt is the hydrochloride while the maleate salt is the preferred organic acid salt.

The term "lower alkyl" as used herein, except as indicated otherwise, is meant to include straight or branched chain hydrocarbons having from 1 to 7 carbon atoms, preferably from 1 to 4 carbon atoms. Methyl is a most preferred lower alkyl group.

The method of administering the compounds of formula I is not critical to the obtention of the indicated antifertility activity. These compounds may therefore be used in the form of conventional pharmaceutical preparations; for example, the aforesaid compounds can be mixed with conventional organic or inorganic, inert pharmaceutical carriers suitable for parenteral or enteral administration, such as, for example, water, gelatin, lactose, starch, magnesium stearate, talc, vegetable oil, gums, polyalkylene glycols, vaseline or the like. They can be administered in conventional pharmaceutical forms, e.g., solid forms, for example, tablets, dragees, capsules, suppositories or the like; or liquid forms, for example, injectable solutions, suspensions or emulsions. Moreover, the pharmaceutical compositions containing compounds described above can be subject to conventional pharmaceutical expedients such as sterilization and can contain conventional pharmaceutical excipients such as preservatives, stabilizing agents, wetting agents, emulsifying agents, salts for the adjustment of osmotic pressure or buffers. The compositions can also contain other biologically active materials if desired.

Another aspect of the invention relates to the use of the instant compounds as chemical sterilants for the control of pest populations. These compounds can be prepared as a pre-mix concentrate containing 1 to 70 wt/% active component in a suitable carrier which can then be blended into foodstuffs or liquids to form bait formulations for the indicated pest. Suitable carriers include flavored or unflavored solid carriers which may be water soluble, e.g., sugars such as sucrose, glucose and the like, or water insoluble such as starch, dicalcium phosphate and the like. Active components which are liquids at normal conditions may be absorbed into suitable porous supports such as calcium silicate, silicic acid, silicon dioxide, calcium carbonate, etc. Hydrophobic forms of the active component, i.e., the free base, may be dissolved in edible vegetable oils. Protected forms of the active component concentrates can be prepared by emulsifying or dispersing such component into a solution of gum of acacia and then spray drying.

The aforesaid concentrates may be employed in preparing suitable bait formulations by blending with liquids, i.e., drinking water which can be flavored with a sugar such as sucrose, or into solid foodstuffs. Suitable foodstuffs useful as bait materials include cereal grain or mixtures such as rat chow or oatmeal which can optionally contain glycerine; animal renderings; fish meal and the like. It is desirable to utilize the aforesaid compounds in a concentration of from about 0.05 to 1 wt./% based on the final bait composition, most preferably in the range of from about 0.1 to 0.5 wt/%. Selection of a particular composition will, of course, depend on the species of pest involved and the average intake of the baited food by the pest in the wild at a single feeding. For example, permanent sterility in male rats can be obtained using single doses of preferred compounds of this invention at 20 mg/rat. This would correspond to a bait composition containing about 0.1 to 0.2 wt/% of the active compound.

Suitable pharmaceutical dosage units for use as orally active antifertility agents in avian or mammalian males can contain from about 0.5 to 1,000 mg. of the aforesaid compounds or corresponding amount of an addition salt thereof in a conventional pharmaceutical oral carrier. Suitable dosage regimens in male mammals for inducing temporary sterility include an oral dosage in the range of from about 0.4 mg/kg per day to about 75 mg/kg per day. Suitable parenteral dosage regimens for this purpose in male mammals comprise from about 0.4 mg/kg per day to about 75 mg/kg per day. Permanent sterility in human males can be obtained by a single oral dosage containing from about 18 mg/kg to about 25 mg/kg of the aforesaid compounds.

It is understood, however, that for any particular subject the specific dosage regimen should be adjusted according to individual needs and the professional judgment of the person administering or supervising the administration of the aforesaid compounds. Dosages will obviously vary with species, duration of treatment and effect intended. Thus, a preferred compound of this invention will cause permanent sterility in male rats at about 6.25 mg/kg/day after 21 days of treatment, while a single oral dose of 20 mg/rat (~100 mg/kg) will also produce this effect. The dosages set forth herein are thus exemplary only and that they do not, to any extent, limit the scope or practice of this invention.

The methods and compositions of the present invention will be more clearly understood by reference to the following examples which are advanced for purposes of illustration only.

EXAMPLE 1

D,L-6-(N-α-pipecolinomethyl)-5-hydroxyindane maleate was tested in immature male rats to determine the effect on the sex organ weights at the indicated oral dosages. The results of these experiments are summarized below in Table 1.

TABLE 1

Effects of D,L-6-(N-α-pipecolinomethyl)-5-hydroxyindane maleate on Sex Organ Weights of Immature Male Rats

| Test Compound (mg/rat/day) | N | Mean Body Weight Initial | Mean Body Weight Final | Testes | Mean Organ Weights (mg) ± S.E. Seminal Vesicles | Ventral Prostate |
|---|---|---|---|---|---|---|
| 0 | 10 | 43 | 102 | 930 ± 30 | 26.5 ± 1.8 | 65.6 ± 3.1 |
| 0.1 | 10 | 43 | 98 | 816 ± 22 | 21.1 ± 1.5 | 59.1 ± 3.7 |
| 0.2 | 9 | 43 | 101 | 806 ± 32 | 24.3 ± 1.5 | 61.9 ± 3.5 |
| 0.4 | 9 | 43 | 100 | 673 ± 29 | 21.1 ± 1.5 | 56.8 ± 4.2 |
| 0 | 10 | 42 | 96 | 869 ± 10 | 26.8 ± 1.8 | 68.3 ± 2.8 |
| 1 | 9 | 43 | 87 | 457 ± 20 | 19.8 ± 1.6 | 47.7 ± 1.5 |
| 2 | 10 | 42 | 87 | 355 ± 13 | 17.0 ± 1.0 | 50.8 ± 5.5 |
| 4 | 10 | 42 | 82 | 335 ± 14 | 16.6 ± 1.1 | 45.4 ± 2.4 |

Charles River CD rats, 22 days old at the beginning of the study, were treated once daily for 10 consecutive days, D,L-6-(N-α-pipecolinomethyl)-5-hydroxyindane maleate was administered orally in 0.2 ml/day ASV. ASV = aqueous suspending vehicle which consists of 0.9% sodium chloride, 0.9% benzyl alcohol, 0.5% carboxymethyl cellulose, and 0.4% polysorbate 80 in distilled water. Underlined means are significantly different from Controls at $p < .05$ or better.

It is seen from the above experiment that oral administration of D,L-6-(N-α-pipecolinomethyl)-5-hydroxyindane maleate to immature male rats resulted in a depression of testes, seminal vesicle and ventral prostate weight. At high dosage levels all three organ weights were depressed, whereas with reduction in dose level there was no effect on prostate weight, erratic effect upon seminal vesicle weight and continued depression of testes weight. This would appear to indicate a greater effect by the compound on the gonad than on the secondary sex organs.

EXAMPLE 2

D,L-6-(N-α-pipecolinomethyl)-5-hydroxyindane maleate was tested for antigonadal activity in immature gerbils, hamsters, guinea pigs and mice. The effect of oral administration of the aforesaid compound in varying dosages is summarized in the following table:

TABLE 2

Effects of D,L-6-(N-α-pipecolinomethyl)-5-hydroxyindane maleate on Testes Weights of Immature Gerbils, Hamsters, Guinea Pigs and Mice

| Species | Test Compound (mg/day) | N | Mean Body Weight grams Initial | Mean Body Weight grams Final | Mean ± S.E. Testes (mg) |
|---|---|---|---|---|---|
| Gerbil | 0 | 10 | 20 | 31 | 212 ± 10 |
|  | 0.5 | 10 | 21 | 32 | 237 ± 30 |
|  | 1.0 | 9 | 20 | 32 | 234 ± 24 |
| Hamster | 0 | 10 | 35 | 56 | 741 ± 19 |
|  | 1. | 10 | 38 | 59 | 549 ± 48 |
|  | 2. | 9 | 37 | 59 | 362 ± 34 |
| Guinea Pig | 0. | 10 | 264 | 332 | 704 ± 96 |
|  | 2.5 | 10 | 270 | 320 | 456 ± 40 |
|  | 5.0 | 10 | 272 | 312 | 413 ± 28 |
| Mouse | 0 | 10 | — | 21 | 111 ± 3 |
|  | 0.1 | 10 | — | 19 | 103 ± 5 |
|  | 0.3 | 9 | — | 18 | 81 ± 4 |
|  | 1.0 | 10 | — | 17 | 50 ± 5 |

D,L-6-(N-α-pipecolinomethyl)-5-hydroxyindane maleate administered orally once daily for 10 consecutive days in 0.2 ml/day ASV. ASV = aqueous suspending vehicle. Underlined means significantly different from Controls at $p < .05$ or better.

TABLE 3

Recovery of Testes Weight Following Ten Days Treatment with
D,L-6-(N-α-pipecolinomethyl)-5-hydroxyindane maleate in the Immature Rat

| Treatment | Days Post Rx | N | Mean Final Body Weight (g) | Mean ±S.E. Testes (mg) |
|---|---|---|---|---|
| Controls | 1 | 8 | 101 | 835 ± 32 |
| Test Compound | 1 | 8 | 102 | 608 ± 30*** |
| Controls | 7 | 8 | 140 | 1294 ± 79 |
| Test Compound | 7 | 7 | 141 | 1011 ± 72*** |
| Controls | 14 | 8 | 185 | 1987 ± 49 |
| Test Compound | 14 | 6 | 181 | 1347 ± 72*** |
| Controls | 21 | 8 | 231 | 2498 ± 92 |
| Test Compound | 21 | 5 | 207 | 1615 ± 141*** |
| Controls | 1 | 10 | 98 | 895 ± 27 |
| Test Compound | 1 | 10 | 95 | 503 ± 35*** |
| Controls | 28 | 6 | 274 | 2901 ± 71 |
| Test Compound | 28 | 5 | 248 | 2292 ± 49*** |
| Controls | 35 | 6 | 289 | 3023 ± 84 |
| Test Compound | 35 | 6 | 288 | 2819 ± 123 |
| Controls | 42 | 6 | 330 | 2707 ± 214 |
| Test Compound | 42 | 6 | 304 | 2760 ± 71 |

***$p<.001$ when compared with corresponding controls.
Charles River CD 22 days old rats treated for 10 consecutive days with 1 mg/rat/day D,L-6-(N-α-pipecolinomethyl)-5-hydroxyindane maleate in 0.2 ml/day ASV administered orally. ASV = aqueous suspending vehicle.

It is seen from the above results that the test compound depressed tests weights in immature hamsters, guinea pigs and mice. Hence the effect on the testes of the compound is not species-specific to the rat. The immature gerbil testes were apparently not susceptible to the test compound.

EXAMPLE 3

This example involves the determination as to whether there is a recovery of normal testes weights in immature rats treated orally with a ten day course of treatment with D,L-6-(N-α-pipecolinomethyl)-5-hydroxyindane maleate. The results of this experiment are summarized below in Table 3.

It is seen that recovery of normal testes weights occurred approximately five weeks after the end of the 10 day course of treatment.

EXAMPLE 4

In this example rats treated with D,L-6-(N-α-pipecolinomethyl)-5-hydroxyindane maleate were further treated with injections of Pregnant Mare's serum gonadotropin (PMS) or Human Chorionic gonadotropin (HCG) to determine their effect on testes weight depression. Results of the experiment are summarized in Table 4.

TABLE 4

Effects of PMS and HCG on Testes Weight Depression by D,L-6-(N-α-pipecolinomethyl)-5-hydroxy-indane maleate and Effects of D,L-6-(N-α-pipecolinomethyl)-5-hydroxyindane maleate on Seminal Vesicle and Ventral Prostate Weight Increase Caused by Stimulation of Endogenous Androgen Secretion by PMS and HCG

| Group | Treatment | N | Mean Body Weight grams Initial | Final | Testes | Seminal Vesicles | Ventral Prostate |
|---|---|---|---|---|---|---|---|
| 1 | Controls | 10 | 45 | 99 | 909 ± 27 | 29.2 ± 2.4 | 69.4 ± 5.3 |
| 2 | Test Compound | 10 | 45 | 92 | 422 ± 20*** | 21.9 ± 1.1* | 46.9 ± 2.8** |
| 3 | PMS | 10 | 45 | 100 | 897 ± 19 | 185.7 ± 8.9*** | 155.1 ± 10.2*** |
| 4 | PMS and Test Compound | 9 | 47 | 99 | 457 ± 18*** | 65.0 ± 5.5*** | 97.4 ± 4.9** |
| 5 | HCG | 9 | 45 | 103 | 975 ± 30 | 185.8 ± 11.6*** | 148.4 ± 6.7*** |
| 6 | HCG and Test Compound | 10 | 45 | 94 | 406 ± 20*** | 52.3 ± 4.6*** | 114.1 ± 5.9*** |

*$p<.05$, $p<.01$, *$p<.001$ when compared with controls.

| Additional "t" tests Groups | Seminal Vesicles | Ventral Prostate |
|---|---|---|
| 3 vs 4 | *** | *** |
| 5 vs 6 | *** | ** |
| 2 vs 4 | *** | *** |
| 2 vs 6 | *** | *** |

Charles River CD rats treated once daily for 10 consecutive days. D,L-6-(N-α-pipecolinomethyl)-5-hydroxy-indane maleate administered orally at 1.5 mg/rat/day in 0.2 ml/day ASV. ASV = aqueous suspending vehicle. PMS administered subcutaneously at 10 units/rat/day in 0.2 ml/day Saline. HCG administered subcutaneously at 10 units/rat/day in 0.2 ml/day Saline.

It is seen that injections of PMS or HCG failed to reverse the testes weight depression produced by treatment with the test compound. The lesser response of the seminal vesicles and ventral prostates of animals given the test compound and gonadotropin compared to those receiving gonadotropin alone indicate that Leydig cell response to stimulation by gonadotropin was abnormal. The Leydig cells were capable of secreting androgen as evidenced by increased weight of secondary sex organs compared to vehicle controls, but the response was significantly less than that of gonadotropin controls. This data indicates that the effect of the test compound was not due to suppression of gonadotropin secretion.

EXAMPLE 5

The experiment of Example 4 was repeated with the exception that the dosage of D,L-6-(N-α-pipecolinomethyl)-5-hydroxyindane maleate was reduced to less than half that of the prior experiment and there was an increase of gonadotropin dosage to three times that of the previous example. Additionally, test animals were dosed with Methallibure, a non-steroidal, non-estrogenic antigonadotropin. The results are summarized in Table 5 below.

TABLE 5

Effects of PMS and HCG on Testes Weight Depression by D,L-6-(N-α-pipecolinomethyl)-5-hydroxy-indane maleate on Seminal Vesicle Weight Increase Caused by Stimulation of Endogenous Androgen Secretion by PMS and HCG. Comparison with Methallibure

| Testes (mg) | − Gonadotropin | + PMS | + HCG |
|---|---|---|---|
| Controls | 931 ± 36 | 1042 ± 25 | 1130 ± 30 |
| Test Compound | 575 ± 49 | 609 ± 22 | 581 ± 28 |
| Methallibure | 358 ± 32 | 1069 ± 32 | 1005 ± 25 |

| Seminal Vesicles (mg) | − Gonadotropin | + PMS | + HCG |
|---|---|---|---|
| Controls | 32.4 ± 3.3 | 252.1 ± 17.0 | 250.6 ± 13.3 |
| Test Compound | 19.3 ± 2.1 | 133.8 ± 6.9 | 127.3 ± 13.9 |
| Methallibure | 10.3 ± 1.0 | 277.8 ± 15.9 | 235.2 ± 16.1 |

Charles River 22 day old rats treated once daily for 10 consecutive days. D,L-6-(N-α-pipecolinomethyl)-5-hydroxy-indane maleate administered orally, 0.7 mg/day in ASV, 0.2 ml/day. Methallibure administered orally 3 mg/day in ASV, 0.2 ml/day. ASV = aqueous suspending vehicle. PMS and HCG at 30 units/day subcutaneously in 0.2 ml/day saline.

The above results show that the reduction of dosage of the test compound did not result in alteration of the depressant effect of the test compound on testes and seminal vesicle weights. The effects of the Methallibure were completely reversed on both parameters by both gonadotropin preparations. This indicates that the test compound produces its results by a different mechanism than Methallibure.

EXAMPLE 6

The purpose of this Example was to test the effect of testosterone on rats which had undergone a testes weight depression by treatment with D,L-6-(N-α-pipecolinomethyl)-5-hydroxyindane maleate (the test compound of the present invention), norethindrone (a steroid antigonadotropin) and Methallibure (a non-steroid antigonadotropin). The results of these experiment are summarized below in Tables 6 and 7.

TABLE 6

Effect of Testosterone on Testes Weight Depression Caused by D,L-6-(N-α-pipecolinomethyl)-5-hydroxy-indane maleate and Norethindrone

| Testes (mg) | − Testosterone | + Testosterone |
|---|---|---|
| Controls | 980 ± 34 | 867 ± 11 |
| Test Compound | 568 ± 25 | 396 ± 31 |
| Norethindrone | 609 ± 57 | 827 ± 20 |

| Seminal Vesicles (mg) | − Testosterone | + Testosterone |
|---|---|---|
| Controls | 38.1 ± 2.9 | 359.3 ± 15.1 |
| Test Compound | 38.2 ± 3.5 | 361.3 ± 20.6 |
| Norethindrone | 31.2 ± 2.8 | 407.6 ± 14.3 |

| Ventral Prostate (mg) | − Testosterone | + Testosterone |
|---|---|---|
| Controls | 69.7 ± 4.3 | 208.0 ± 21.7 |
| Test Compound | 61.2 ± 6.7 | 191.9 ± 4.9 |
| Norethindrone | 51.9 ± 4.7 | 195.7 ± 18.6 |

Charles River CD 22 day old rats treated once daily for 10 consecutive days. D,L-6-(N-α-pipecolinomethyl)-5-hydroxy-indane maleate and Norethindrone administered orally at 1 mg/rat/day. Testosterone administered subcutaneously at 1 mg/rat/day. ASV vehicle. ASV = aqueous suspending vehicle.

TABLE 7

Effect of Testosterone on Testes Weight Depression Caused by
D,L-6-(N-α-pipecolinomethyl)-5-hydroxy-indane maleate and Methallibure Testes (mg)

|  | − Testosterone | + Testosterone |
|---|---|---|
| Controls | 461 ± 15 | 589 ± 33 |
| Test Compound | 142 ± 4 | 145 ± 5 |
| Methallibure | 195 ± 14 | 549 ± 35 |

Seminal Vesicles (mg)

|  | − Testosterone | + Testosterone |
|---|---|---|
| Controls | 16.5 ± 4.5 | 264.5 ± 15.8 |
| Test Compound | 11.1 ± 0.6 | 254.2 ± 10.3 |
| Methallibure | 9.2 ± 0.8 | 209.9 ± 14.0 |

Ventral Prostate (mg)

|  | − Testosterone | + Testosterone |
|---|---|---|
| Controls | 40.9 ± 4.5 | 151.8 ± 10.6 |
| Test Compound | 36.2 ± 3.7 | 128.0 ± 8.2 |
| Methallibure | 23.1 ± 2.7 | 150.8 ± 9.6 |

A and D rats (40 grams body weight) treated once daily for 10 consecutive days. D,L-6-(N-α-pipecolinomethyl)-5-hydroxy-indane maleate and Methallibure administered orally at 1 mg/rat/day. Testosterone administered subcutaneously at 1 mg/rat/day. ASV vehicle. ASV = aqueous suspending vehicle.

The results indicate that testosterone failed to reverse the testes weight depression caused by the test compound of the present invention but did reverse the testes weight effects of Norethindrone and Methallibure. The seminal vesicles and ventral prostates of animals treated by the test compound of this invention responded normally to testosterone stimulation which would indicate that the reduction in the weights of these organs obtained in prior experiments with the test compound were probably not due to a direct action of the compound on the secondary sex organs, but more likely were the results of reduced androgen production and/or secretion by the testes of such treated animals. Thus the mechanism of action of the test compound differs from that of the known antigonadotropins.

EXAMPLE 7

This example was for the purpose of determining whether large doses of Vitamin E and methionine could reverse the testicular effects of D,L-6-(N-α-pipecolinomethyl)-5-hydroxyindane maleate. It is known that testes weight depression and antispermatogenic effects can be produced in rats by Vitamin E deficiency. Interference with methionine metabolism can also produce such effects. The results of this experiment are summarized below in Table 8.

TABLE 8

Effects of Tocopherol Acetate and Methionine on Testes Weight
Depression by D,L-6-(N-α-pipecolinomethyl)-5-hydroxy-indane maleate

| Testes (mg) |  | + Toc. Ac. | + Methionine |
|---|---|---|---|
| Control | 1028 ± 35 | 990 ± 45 | 955 ± 31 |
| Test Compound | 648 ± 53 | 547 ± 28 | 683 ± 56 |

Charles River CD 22 day old rats treated once daily for 10 consecutive days. D,L-6-(N-α-pipecolinomethyl)-5-hydroxy-indane maleate at 1 mg/rat/day, DL-Tocopherol Acetate at 10 mg/rat/day, and DL-Methionine at 10 mg/rat/day. All compounds administered orally in sesame oil vehicle.

It is seen from the results of the above table that administration of tocopherol acetate (Vitamin E acetate) and methionine at high dosage failed to reverse the effects of the test compound on the testes of the treated rats.

EXAMPLE 8

The purpose of this Example is to compare the spermatogenesis inhibition and/or testes weight depression of D,L-6-(N-α-pipecolinomethyl)-5-hydroxy-indane maleate with known compounds having these activities. The results are described in Table 9 which follows.

TABLE 9

Comparison of Effects of WIN 18446,*Nitrofurazone, Methallibure, Diethylstilbestrol and D,L-6-(N-α-pipecolinomethyl)-5-hydroxy-indane maleate on Sex Organ Weights in Adult Male Rats

| Treatment | N | Mean Body Weight grams Initial | Final | Testes | Seminal Vesicles | Ventral Prostate |
|---|---|---|---|---|---|---|
| Vehicle Controls ASV, 0.2 ml/day | 8 | 158 | 308 | 3004 ± 89 | 435 ± 43 | 358 ± 38 |
| WIN 18446* 50 mg/kg/day | 7 | 165 | 280 | 2214 ± 170 | 455 ± 36 | 293 ± 17 |
| Nitrofurazone 50 mg/kg/day | 7 | 160 | 290 | 1414 ± 179 | 409 ± 21 | 350 ± 29 |
| Methallibure 50 mg/kg/day | 4 | 157 | 224 | 2072 ± 189 | 49 ± 13 | 46 ± 13 |
| Diethylstilbestrol 50 mg/kg/day | 7 | 160 | 162 | 1128 ± 208 | 51 ± 4 | 37 ± 6 |
| Test Compound 50 mg/kg/day | 8 | 163 | 282 | 868 ± 54 | 255 ± 19 | 178 ± 17 |

Compounds administered orally once daily for 21 consecutive days. Underlined means are significantly different from controls at $p < .05$ or better. ASV = aqueous suspending vehicle.
*WIN 18446 = N,N'-bis-(dichloroacetyl)-1,3-octamethylenediamine.

It will be seen from the above table that the test compound of this invention had a greater effect on testes weight, but a lesser effect on ventral prostate and seminal vesicle weight than the other indicated compounds.

EXAMPLE 9

This Example demonstrates the effect on testes weight reduction in adult rats by the oral administration of D,L-6-(N-α-pipecolinomethyl)-5-hydroxyindane maleate at low dosage rates. This experiment is summarized below in Table 10.

TABLE 10

Effects of Duration of Oral Treatment with D,L-6-(N-α-pipecolinomethyl)-5-hydroxyindane maleate on Sex Organ Weights of Adult Male Rats

| Test Compound mg/kg/day | X Days | N | Initial | Final | Testes | Seminal Vesicles | Ventral Prostate |
|---|---|---|---|---|---|---|---|
| 0 | 3 | 6 | 212 | 232 | 2473 ± 80 | 332 ± 19 | 242 ± 17 |
| 1 | 3 | 6 | 204 | 243 | 2322 ± 134 | 290 ± 33 | 238 ± 19 |
| 2 | 3 | 6 | 207 | 222 | 2109 ± 78 | 302 ± 45 | 236 ± 23 |
| 0 | 6 | 6 | 209 | 248 | 2484 ± 79 | 402 ± 51 | 266 ± 12 |
| 1 | 6 | 6 | 213 | 233 | 1882 ± 113 | 275 ± 40 | 190 ± 21 |
| 2 | 6 | 6 | 206 | 246 | 2034 ± 152 | 372 ± 19 | 222 ± 18 |
| 0 | 9 | 6 | 209 | 280 | 2582 ± 40 | 362 ± 20 | 280 ± 24 |
| 1 | 9 | 6 | 202 | 278 | 1826 ± 167 | 331 ± 25 | 266 ± 19 |
| 2 | 9 | 6 | 201 | 268 | 1701 ± 143 | 312 ± 32 | 238 ± 36 |
| 0 | 12 | 6 | 208 | 292 | 2872 ± 131 | 694 ± 52 | 365 ± 29 |
| 1 | 12 | 6 | 201 | 287 | 2035 ± 376 | 494 ± 55 | 322 ± 31 |
| 2 | 12 | 6 | 205 | 280 | 1384 ± 132 | 493 ± 68 | 338 ± 10 |
| 0 | 15 | 5 | 209 | 321 | 2810 ± 80 | 544 ± 37 | 388 ± 12 |
| 1 | 15 | 3 | 193 | 305 | 2162 ± 473 | 496 ± 57 | 360 ± 31 |
| 2 | 15 | 4 | 206 | 325 | 1477 ± 255 | 499 ± 53 | 296 ± 26 |
| 0 | 18 | 5 | 204 | 321 | 2984 ± 83 | 488 ± 53 | 433 ± 29 |
| 1 | 18 | 3 | 199 | 331 | 2142 ± 342 | 557 ± 59 | 486 ± 14 |
| 2 | 18 | 4 | 207 | 302 | 1174 ± 142 | 402 ± 67 | 370 ± 63 |
| 0 | 21 | 6 | 201 | 350 | 3078 ± 60 | 654 ± 46 | 554 ± 61 |
| 1 | 21 | 4 | 187 | 333 | 1736 ± 330 | 534 ± 67 | 424 ± 38 |
| 2 | 21 | 5 | 205 | 321 | 1588 ± 340 | 497 ± 24 | 449 ± 60 |

Underlined means are statistically different from Controls at $p < .05$ or better.

The results of this experiment indicate that 2 mg/kg/day orally was sufficient to manifest a reduction in testes weight in adult rats. Treatment at this dosage failed to cause a consistent effect upon the seminal vesicle and ventral prostate weights when animals were examined at three-day intervals up to 21 days. At 1 mg/kg/day the effect upon the testes was erratic, but consistent reduction in testes weight at this dose occurred with 18 and 21 days of treatment.

EXAMPLE 10

This example demonstrates the effect of treatment with D,L-6-(N-α-pipecolinomethyl)-5-hydroxy-indane maleate on testes weight in hypophysectomized rats. The results of this experiment are summarized in Table 11 below.

TABLE 11

Effect of D,L-6-(N-α-pipecolinomethyl)-5-hydroxy-indane maleate on Testes Weight in Hypophysectomized Rats

| Days of Treatment | Mean Testes Weight (mg) + S.E. Controls | Test Compound |
|---|---|---|
| 1 | 2431 ± 39 | 2329 ± 58 |

TABLE 11-continued

Effect of D,L-6-(N-α-pipecolinomethyl)-5-hydroxy-indane maleate on
Testes Weight in Hypophysectomized Rats

| Days of Treatment | Mean Testes Weight (mg) + S.E. | | |
|---|---|---|---|
| | Controls | Test Compound | |
| 4 | 2212 ± 67 | 1412 ± 61 | p<.001 |
| 7 | 2015 ± 72 | 937 ± 51 | p<.001 |
| 10 | 1562 ± 54 | 677 ± 14 | p<.001 |
| 13 | 1434 ± 117 | 558 ± 24 | p<.001 |
| 16 | 995 ± 138 | 498 ± 23 | p<.001 |

D,L-6-(N-α-pipecolinomethyl)-5-hydroxy-indane maleate administered orally at 2 mg/kg/day beginning one day after hypophysectomy. Rats 56 days old when pituitary was removed with 6 to 9 rats per group.

It is seen from the results contained in the above table that the test compound was effective in reducing testes weight in hypophysectomized rats at a rate greater than that due to the effects of pituitary absence. Consequently, the presence of gonadotropin is not a necessary condition for the activity of the test compound. The compound has a direct effect upon the testes. The observations with non-hypophysectomized rats in previous experiments would suggest that the mechanism of action of the test compound probably involves interference with those biochemical pathways which are normally responsive to the gonadotropin stimulation.

EXAMPLE 11

This example demonstrates the effectiveness of D,L-6-(N-α-pipecolinomethyl)-5-hydroxyindane maleate as an antigonadotropin agent in adult rabbits. The results of this experiment are summarized below in Table 12.

TABLE 12

Effect of D,L-6-(N-α-pipecolinomethyl)-5-hydroxy-indane maleate on Testis Weight in Adult Rabbits One testis was removed and weighed prior to initiation of treatment (Day 1). Rabbits were then treated once daily with D,L-6-(N-α-pipecolinomethyl)-5-hydroxy-indane maleate in 0.2 ml/day ASV administered subcutaneously. Duration of treatment was ten consecutive days. On day 11 the remaining testis was removed and weighed.

| Rabbit | Dose/Day | Body Weight grams | | Testis Weight (mg) | | |
|---|---|---|---|---|---|---|
| | | Initial | Final | Day 1 | Day 11 | % |
| 1 | 10 mg | 3425 | 3082 | 3266 | 2187 | −33 |
| 2 | 10 mg | 4665 | 3975 | 3437 | 2112 | −39 |
| 3 | 10 mg | 4900 | 4770 | 3423 | 2341 | −32 |
| 4 | 40 mg | 5230 | 4355 | 3368 | 1118 | −67 |
| 5 | 40 mg | 4150 | 3933 | 3805 | 2119 | −44 |
| 6 | 40 mg | 4660 | 4150 | 3988 | 1620 | −59 |
| 7 | 40 mg | 4075 | 3415 | 2240 | 1514 | −32 |

It can be seen from the above table that the test compound was effective in depressing testes weights in adult rabbits.

EXAMPLE 12

Adult male rats were treated with D,L-6-(N-α-pipecolinomethyl)-5-hydroxy-indane maleate at oral dosages in the range of 6.25 to 50 mg/kg/day for 21 days. The results of this experiment are summarized in Table 13 below.

TABLE 13

Effect of D,L-6-(N-α-pipecolinomethyl)-5-hydroxy-indane maleate on Organ Weights of Adult Male Rats

| Parameter | ASV 0.2 ml/d | Test Compound 6.25 mg/kg/d | Test Compound 12.5 mg/kg/d | Test Compound 25 mg/kg/d | Test Compound 50 mg/kg/d |
|---|---|---|---|---|---|
| N | 6 | 3 | 4 | 6 | 4 |
| Initial Body Weight (g) | 186 | 185 | 204 | 196 | 185 |
| Final Body Weight (g) | 326 | 339 | 346 | 349 | 266 |
| Weight Gain (g) | 140 | 154 | 142 | 153 | 81 |
| Testes (mg) | 3042 ± 87 | 1128 ± 50 | 1021 ± 23 | 1075 ± 66 | 880 ± 62 |
| Seminal Vesicles (mg) | 493 ± 25 | 541 ± 58 | 410 ± 47 | 435 ± 26 | 352 ± 60 |
| Ventral Prostate (mg) | 402 ± 18 | 393 ± 16 | 304 ± 35 | 296 ± 25 | 198 ± 42 |
| Adrenals (mg) | 49.6 ± 2.9 | 49.0 ± 3.0 | 51.4 ± 3.4 | 45.6 ± 7.2 | 50.1 ± 1.9 |
| Thymus (mg) | 486 ± 68 | 582 ± 52 | 567 ± 34 | 675 ± 44 | 489 ± 35 |
| Thyroid (mg) | 18.4 ± 1.0 | 18.1 ± 1.3 | 20.2 ± 1.8 | 18.0 ± 0.9 | 16.0 ± 1.8 |
| Pituitary (mg) | 10.7 ± 0.7 | 11.7 ± 0.3 | 12.9 ± 1.2 | 11.9 ± 0.7 | 10.5 ± 0.2 |

D,L-6-(N-α-pipecolinomethyl-5-hydroxy-indane maleate administered orally once daily for 21 consecutive days. Underlined means are significantly different from Controls at p<.05 or better. N = number of rats in treatment group.

It is seen from the above table that at all dosage levels tested a reduction in testes and ventral prostate weights was obtained. Reduction in body weight gain occurred at the 50 mg/kg dose level. No effects were apparent on adrenal, thymus, thyroid and pituitary weights even at the highest dosage level. The absence of thymus involution and adrenal hypertrophy indicates a lack of significant toxicity.

Half of the animals in each of the groups of Table 13 were not autopsied following the 21 day treatment period but were used for determination of fertility. As shown in Table 14 below all of these rats were still sterile at the termination of the experiment 132 days post-treatment. There was no apparent effect on libido or sexual activity, since normal mounting behavior was observed.

TABLE 14

Effect of D,L-6-(N-α-pipecolinomethyl)-5-hydroxy-indane maleate on Fertility of Male Rats

| Test Compound mg/kg/day | N | Comments |
|---|---|---|
| 6.25 | 3 | All rats still sterile 132 days post treatment. |
| 12.5 | 4 | All rats still sterile 132 days post treatment. |
| 25. | 6 | All rats still sterile 132 days post treatment. |
| 50. | 5 | All rats still sterile 132 days post treatment. |

D,L-6-(N-α-pipecolinomethyl)-5-hydroxy-indane maleate administered orally once daily for 21 consecutive days. Males then permitted to cohabit with untreated females (1 male to 2 females). Females observed for pregnancy thereafter until 2 weeks after autopsy of males at 132 days post treatment.

EXAMPLE 13

This example utilized the procedure of Example 12 with the exception that the daily dosages were reduced to the range of 0.375 – 3 mg/kg/day. Depression of testes weight and ventral prostate weight after 21 days were observed at the 1.5 and 3 mg/kg/day levels. The effect of these treatments on the fertility of the male rats is summarized below in Table 15.

TABLE 15

Effects of D,L-6-(N-α-pipecolinomethyl)-5-hydroxy-indane maleate on Fertility of Male Rats Treated Once Daily for 21 Consecutive Days

| Test Compound mg/kg/day | No. of Treated Males | No. of Untreated Females | Number of females with Fertile Matings During Post Treatment Week | | | | | | | | | | | |
|---|---|---|---|---|---|---|---|---|---|---|---|---|---|---|
| | | | 1 | 2 | 3 | 4 | 5 | 6 | 7 | 8 | 9 | 10 | 11 | 12 |
| 0 | 6 | 13 | 9 | 2 | 2 | | | | | | | | | |
| 0.375 | 6 | 12 | 8 | 3 | 1 | | | | | | | | | |
| 0.75 | 6 | 12 | 4 | 2 | 2 | 1 | 0 | 1 | 1 | 0 | 0 | 1 | | |
| 1.5 | 5 | 10 | 1 | 1 | 6 | 2 | | | | | | | | |
| 3.0 | 6 | 12 | | | | | | | | 4 | 1 | 1 | 2 | * |

*4 females not pregnant 12 weeks post treatment of males with D,L-6-(N-α-pipecolinomethyl)-5-hydroxy-indane maleate.

It is seen from the above table that at the 3 mg/kg dose level fertility resumed approximately 50 to 60 days post treatment. However, even at the 1.5 mg/kg dose level there appeared to be some interference with normal fertility.

EXAMPLE 14

This example demonstrates the effect on fertility of male rats treated at dosages of 2 and 4 mg/kg/day from 1 to 14 days with D,L-6-(N-α-pipecolinomethyl)-5-hydroxyindane maleate. The effects on fertility are summarized below in Table 16.

TABLE 16

Effects of Oral Administration of D,L-6-(N-α-pipecolinomethyl)-5-hydroxy-indane maleate, 2 and 4 mg/kg/day on Fertility of Male Rats

| No. of Days Treatment 2 mg/kg/day | No. of Males | No. of Females | Number of Females with Fertile Matings During Post Treatment Week | | | | | | | | | | | | | |
|---|---|---|---|---|---|---|---|---|---|---|---|---|---|---|---|---|
| | | | 1 | 2 | 3 | 4 | 5 | 6 | 7 | 8 | 9 | 10 | 11 | 12 | 13 | 14 |
| 1 | 15 | 45 | 18 | 11 | 6 | 4 | 3 | 0 | 0 | 0 | 1 | 0 | 0 | 0 | 0 | 0 |
| 4 | 15 | 45 | 17 | 6 | 3 | 5 | 3 | 4 | 1 | 0 | 3 | 0 | 0 | 0 | 0 | 0 |
| 7 | 15 | 45 | 10 | 4 | 1 | 2 | 1 | 2 | 1 | 2 | 7 | 3 | 2 | 4 | 1 | 0 |
| 14 | 15 | 45 | 2 | 0 | 1 | 2 | 4 | 2 | 2 | 7 | 8 | 7 | 6 | 3 | 0 | 1 |
| 4 mg/kg/day | | | | | | | | | | | | | | | | |
| 1 | 15 | 45 | 20 | 4 | 7 | 2 | 2 | 0 | 2 | 1 | 1 | 0 | 1 | 2 | 0 | 1 |
| 4 | 15 | 45 | 16 | 5 | 0 | 1 | 3 | 1 | 3 | 2 | 6 | 2 | 1 | 1 | 0 | 0 |
| 7 | 15 | 45 | 20 | 0 | 0 | 2 | 0 | 0 | 1 | 0 | 3 | 3 | 10 | 4 | 2 | 0 |
| 14 | 15 | 45 | 0 | 1 | 0 | 1 | 1 | 1 | 1 | 3 | 10 | 2 | 7 | 6 | 1 | 1 |

Male rats treated with D,L-6-(N-α-pipecolinomethyl)-5-hydroxy-indane maleate for number of days indicated and permitted to cohabit with untreated females beginning 24 hours after the last treatment. Ratio of males to females = 1 to 3. Females observed thereafter for pregnancy.

As seen from the above table there is obvious interference with normal fertility at the 2 and 4 mg/kg dosage levels after 14 days of treatment.

EXAMPLE 15

This example demonstrates the effectiveness of a single oral administration of D,L-6-(N-α-pipecolinomethyl)-5-hydroxyindane maleate in inducing sterility in male rats. The effect of one administration of test compound on the sex organ weights of rats were determined 65 days post treatment (the time required for one complete spermatogenic cycle in the rat). These results are summarized below in Table 17.

TABLE 17

Effects of One Oral Administration of D,L-6-(N-α-pipecolinomethyl)-5-hydroxy-indane maleate on Sex Organ Weights Measured 65 days Post Treatment

| Test Compound mg/rat | N | Mean Body Weight grams Initial | Mean Body Weight grams Final | Mean Organ Weight (mg) Standard Error Testes | Mean Organ Weight (mg) Standard Error Seminal Vesicles | Mean Organ Weight (mg) Standard Error Ventral Prostate |
|---|---|---|---|---|---|---|
| 0 | 17 | 156 | 473 | 3371 ± 70 | 957 ± 43 | 742 ± 25 |
| 5 | 9 | 148 | 446 | 1409 ± 134*** | 927 ± 50 | 666 ± 49 |
| 10 | 7 | 156 | 484 | 1498 ± 114*** | 1064 ± 49 | 835 ± 46 |
| 20 | 9 | 154 | 487 | 1125 ± 78 *** | 1018 ± 105 | 639 ± 83 |
| 40 | 5 | 148 | 478 | 1315 ± 147*** | 1031 ± 68 | 647 ± 60 |
| 80 | 6 | 153 | 453 | 1077 ± 40 *** | 1011 ± 62 | 557 ± 58** |

Water vehicle, 0.2 ml/rat p.o.
**p <.01
***p <.001 compared to controls.

It is evident from the above table that significant antigonadal activity was evidenced by the single oral administration of the test compound at oral dosage levels utilized above. The effects of the foregoing single oral administration of the test compound on the fertility of male rats beginning co-habitation with untreated females 65 days post-drug administration was also evaluated. The results are summarized below in Table 18.

TABLE 18

Effects of One Oral Administration of D,L-6-(N-α-pipecolinomethyl)-5-hydroxy-indane maleate on Fertility of Male Rats Beginning Cohabitation with Untreated Females 65 Days Post Treatment

| Test Compound mg/rat | No. of Males | No. of Females | Number of Females with Fertile Matings During Cohabitation Weeks Beginning 65 Days Post Treatment 1 | 2 | 3 | 4 | 5 | 6 |
|---|---|---|---|---|---|---|---|---|
| 5 | 10 | 20 | 10 | 2 | 3 | 1 | 1 | 0 |
| 10 | 8 | 16 | 4 | 2 | 0 | 0 | 0 | 0 |
| 20 | 9 | 18 | 0 | 0 | 0 | 0 | 0 | 1 |
| 40 | 6 | 12 | 0 | 0 | 0 | 0 | 0 | 0 |
| 80 | 6 | 12 | 0 | 0 | 0 | 0 | 0 | 0 |

It is apparent from the above, that one feeding of test compounds at a suitable dosage level, e.g., above about 20 mg/rat, would appear to be sufficient to produce a permanent sterility in the male rat.

EXAMPLE 16

This Example describes a test of the antigonadal activity of compounds of formula I in immature rats. The compounds were dissolved or suspended in an aqueous vehicle (0.9% NaCl, 0.9% benzyl alcohol, 0.5% carboxymethylcellulose, and 0.4% Tween 80 in distilled water) and administered orally to immature male rats (40–50 grams body weight) for 10 consecutive days. Testes weights (mg/100 g.) were determined at autopsy and the percent difference in mean weight from concurrently-run, vehicle treated controls was calculated. Ten rats per group were used. The results of this experiment are summarized in Table 19 below.

TABLE 19

| Compound | Dose mg/rat/day | % Diff. Testes |
|---|---|---|
| (indane with OH and CH₂N-piperidine, ·HCl) | 1 | −29 |
| | 2 | −40 |
| (indane with CH₂-piperidine, OH, CH₂N-piperidine, ·2HCl) | 1 | −13 |
| | 2 | −40 |
| (dimethylphenol with CH₂N-piperidine) | 1 | −15 |
| | 2 | −25 |

TABLE 19-continued

| Compound | Dose mg/rat/day | % Diff. Testes |
|---|---|---|
| [2-(2-methylpiperidin-1-ylmethyl)-4,5-dimethylphenol · (CHCOOH)₂] | 1 | −49 |
| DL [6-(2-methylpiperidin-1-ylmethyl)-5-hydroxyindan · (CHCOOH)₂] | 0.1<br>0.2<br>0.4<br>1<br>2<br>4 | −9<br>−13<br>−15<br>−43<br>−55<br>−55 |
| [2-(3-methylmorpholin-4-ylmethyl)-4,5-dimethylphenol · (CHCOOH)₂] | 1<br>2<br>4 | −19<br>−22<br>−45 |
| [2-(2-piperidin-1-ylethyl)-4,5-dimethylphenol · HCl] | 1<br>2 | −7<br>−37 |
| [6-(3-methylmorpholin-4-ylmethyl)-5-hydroxyindan · HCl] | 1<br>2<br>4 | −21<br>−16<br>−31 |
| [4,6-bis(2-methylpiperidin-1-ylmethyl)-5-hydroxyindan] | 2 | −52 |

TABLE 19-continued

| Compound | Dose mg/rat/day | % Diff. Testes |
|---|---|---|
| l-enantiomer (indane-OH with CH₂N-piperidine-CH₃, ·CHCOOH/CHCOOH) | 0.5 | −30 |
|  | 1 | −35 |
|  | 2 | −44 |
| d-enantiomer (indane-OH with CH₂N-piperidine-CH₃, ·CHCOOH/CHCOOH) | 0.5 | −12 |
|  | 1 | −19 |
|  | 2 | −37 |

The results in the above table demonstrate the oral antigonadal activity of the compounds of formula I in the immature rat.

EXAMPLE 17

This example demonstrates the effect of D,L-6-(N-α-pipecolinomethyl)-5-hydroxyindane maleate on the testes of avian males. The test compound was administered orally to adult male pigeons for 10 working days. The results of this experiment are summarized in Table 20.

TABLE 20

| Treatment | No. of Pigeons | Mean Body Weight Grams Initial | Mean Body Weight Grams Final | Mean Testes Weight ± S.E. (mg) |
|---|---|---|---|---|
| Vehicle Controls | 7 | 399 | 381 | 2385 ± 243 |
| Test Compound, 1 mg. | 8 | 364 | 347 | 1450 ± 148** |
| Test Compound, 5 mg. | 7 | 364 | 341 | 1505 ± 97** |

**p <.01 when compared to controls.

Histological examination of testes sections from treated pigeons showed significant decreases in all spermatogenic cells. Thus, D,L-6-(N-α-pipecolinomethyl)-5-hydroxyindane maleate is seen to be an effective anti-testicular compound in the adult pigeon male.

EXAMPLE 18

Capsule Formulation

|  | Per Capsule |
|---|---|
| D,L-6-(N-α-pipecolinomethyl)-5-hydroxyindane maleate | 50 mg. |
| Lactose, U.S.P. | 125 mg. |
| Corn Starch, U.S.P. | 30 mg. |
| Talc, U.S.P. | 5 mg. |
| Total Weight | 210 mg. |

Procedure:

1. D,L-6-(N-α-pipecolinomethyl)-5-hydroxyindane maleate was mixed with lactose and corn starch in a suitable mixer.
2. The mixture was further blended by passing through a Fitzpatrick Comminuting Machine with No. 1A screen with knives forward.
3. The blended powder was returned to the mixer, the talc added and blended thoroughly.
4. The mixture was filled into No. 4 hard shell gelatin capsules on a Parke Davis capsulating machine.

EXAMPLE 19

Tablet Formulation
250 mg.

|  | Per Tablet |
|---|---|
| D,L-6-(N-α-pipecolinomethyl)-5-hydroxyindane maleate | 250 mg. |
| Dicalcium Phosphate Dihydrate, Unmilled | 235 mg. |
| Corn Starch | 70 mg. |
| FD&C Yellow No. 5 — Aluminum Lake 25% | 2 mg. |
| Durkee 117 | 25 mg. |
| Calcium Stearate | 3 mg. |
| Total Weight | 585 mg. |

Procedure:

1. All the ingredients were mixed thoroughly and Fitzed (Model D) using a No. 1A screen, medium speed.
2. The mixture was remixed and slugged.
3. The slugs were screened on an Oscillator through a No. 14 mesh screen and compressed on an "E" machine.

EXAMPLE 20

Tablet Formulation

| | Per Tablet |
|---|---|
| D,L-6-(N-α-pipecolinomethyl)-5-hydroxyindane maleate | 500 mg. |
| Corn Starch | 30 mg. |
| Lactose | 88 mg. |
| Gelatin | 12 mg. |
| Talcum | 15 mg. |
| Magnesium Stearate | 5 mg. |
| Total Weight | 650 mg. |

Procedure:

1. D,L-6-(N-α-pipecolinomethyl)-5-hydroxyindane maleate and lactose were thoroughly mixed in suitable blending equipment and granulated with a 10% gelatin solution.
2. The moist mass was passed through a No. 12 screen, and the granules were dried on paper lined trays overnight.
3. The dried granules were passed through a No. 14 screen and placed in a suitable mixer. The talcum and magnesium stearate were added and blended.
4. The granulation was compressed into tablets weighing approximately 650 mg. each, using punches having an approximate diameter of 12.7 mm (½"). The final tablet thickness was about 5.1 mm.

EXAMPLE 21

Capsule Formulation

| | Per Capsule |
|---|---|
| D,L-6-(N-α-pipecolinomethyl)-5-hydroxyindane maleate | 250 mg. |
| Lactose | 60 mg. |
| Corn Starch | 35 mg. |
| Magnesium Stearate | 5 mg. |
| Total Weight | 350 mg. |

Procedure:

1. All of the ingredients were mixed until thoroughly blended in a suitable size container.
2. The powder was filled into No. 2, two piece, hard shell gelatin capsules to an approximate fill weight of 350 mg. using a Parke Davis capsulating machine. (Any similar type machine may be used.)

EXAMPLE 22

Parenteral Formulation

Each 1 cc ampul contains:

| | Per cc |
|---|---|
| D,L-6-(N-α-pipecolinomethyl)-5-hydroxyindane maleate | 51.0 mg. (2% excess) |
| Methyl Paraben, U.S.P. | 1.8 mg. |
| Propyl Paraben, U.S.P. | 0.2 mg. |
| Water for Injection, U.S.P. | q.s. ad 1.0 cc. |

Procedure (For 10,000 cc):

1. In a clean glass or glass-lined vessel, 8,000 cc. of Water for Injection were heated to 90°C. It was then cooled to 50°–60°C, and 18 gms of methyl paraben and 2 gms of propyl paraben were added and dissolved with stirring. The solution was then allowed to cool to room temperature.
2. The 51.0 gms. of D,L-6-(N-α-pipecolinomethyl-5-hydroxyindane maleate were added under an atmosphere of nitrogen and stirred until completely dissolved.
3. Sufficient Water for Injection was then added to make a total volumn of 10,000 cc.
4. This solution was then filtered through an 02 Selas candle, filled into suitable size ampuls, gassed with nitrogen and sealed. It was autoclaved at 10 lbs. PSI for 30 minutes.

EXAMPLE 23

Rodent Drinking Water Solution 0.1%
Composition Per Liter of Solution:

| | |
|---|---|
| D,L-6-(N-α-pipecolinomethyl)-5-hydroxyindane maleate | 1.0 gm. |
| Sucrose | 48.0 gm. |
| Demineralized Water | q.s. ad 1.0 liters |

Procedure:

1. A 1,000 liter batch was made by dissolving 48 kilos of sucrose in 950 liters of water in a suitable sized mixing tank.
2. One kilo of D,L-6-(N-α-pipecolinomethyl)-5-hydroxyindane maleate was added with stirring until dissolved.
3. Water was added to bring the solution up to 1,000 liters.

EXAMPLE 24

Rodent Dry Bait 0.1 %

| | |
|---|---|
| D,L-6-(N-α-pipecolinomethyl)-5-hydroxyindane maleate | 0.1% |
| *Liquid Petrolatum | 4.8% |
| Sucrose | 4.8% |
| Breakfast Rolled Oats | 90.3% |

*The liquid petrolatum shall be medicinal grade mineral oil, with a specific gravity of not less than 0.83 nor more than 0.86.

Procedure:

1. The rolled oats were loaded into a suitable liquid solids blender.
2. The sucrose and D,L-6-(N-α-pipecolinomethyl)-5-hydroxyindane maleate were suspended in the liquid petrolatum.
3. This suspension was then pump fed and sprayed onto the oats with continuous mixing until the resultant product was homogenous.

EXAMPLE 25

4.9 G. (0.02 mol) of 6-(2-methylpiperidino)methyl-5-indanol were dissolved in 10 ml. of isopropanol and the solution was treated with a mixture prepared from 4 g. (0.04 mol) of 2-methylpiperidine, 3 ml. (0.04 mol) of 40% formaldehyde solution and 10 ml. of isopropanol. The mixture was boiled under reflux for 17 hours, the solvent was removed by evaporation and the residue was distilled to yield 4.7 g. of 4,6-bis(2-methylpiperidino)methyl-5-indanol as a viscous gum. Boiling point ca 150°C. (air-bath temperature)/0.005 mmHg.

EXAMPLE 26

A solution of 13.42 g. of 5-indanol in 40 cc. of ethanol was treated first with the dropwise addition of 34.08 g. of piperidine and then with 31.6 g. of 37.4% formaline. An exothermic reaction was evidenced during both additions. After addition was complete the mixture was refluxed on a steam bath for two hours. The solvent was removed in vacuo and the residue dissolved in ether. The ether extract was washed with water to remove excess piperidine. The ether was then extracted in portions with a total of 240 cc. 3N HCl. The acid aqueous layer was made basic with 140 cc. of concentrated $NH_4OH$ and an oil separated. The mixture was extracted 6 times with ether. The combined ether extracts after water wash was treated with activated charcoal and filtered. The ether filtrate was dried over sodium sulfate in the presence of HCl gas to produce a sticky solid precipitate. The ether was decanted from the solid precipitate and the solid was dissolved in 200 cc. of water treated with activated charcoal and filtered. After washing the charcoal with additional water the combined aqueous filtrate was extracted with three portions of ether and the resulting aqueous layer was then made basic with 140 cc. of concentrated $NH_4OH$. The basic aqueous solution was extracted seven times with ether. The combined ether extracts after water washing were dried over sodium sulfate. Addition of HCl gas yielded a sticky precipitate. The ether was decanted off and the residue was dissolved in ethanol and the ethanol removed under reduced pressure. This procedure was repeated four times. After standing overnight overnight at room temperature under isopropanol there was obtained after filtration 31 g. (77.2%) of 4,6-bis(1-piperidylmethyl)-5-indanol dihydrochloride melting at 211°–218° (dec.). Recrystallization from isopropanol and ethyl acetate followed by recrystallization from ethanol and ether yielded pure product (22.79 g. - 56.8%) melting at 219°–220.5° (dec.).

Calcd. for $C_{21}H_{32}N_2O·2HCl$: C, 62.82; H, 8.54; N, 6.09. Found: C, 62.84; H, 8.20; N, 7.07.

The above dihydrochloride can be converted into the free base as follows. A total of 150.3 g. of the aforesaid dihydrochloride was dissolved in 300 cc. of water. The aqueous solution was extracted three times with ether. The combined ether extracts were washed once with water. The aqueous solution under water wash were combined and made basic with 150 cc. of concentrated $NH_4OH$. This solution was allowed to stand overnight at room temperature and the resulting crystals were filtered off and washed with 100 cc. of water. There was obtained 113.69 g. of crude 4,6-bis-(1-piperidylmethyl)-5-indanol melting at 80°–100°. The crude free base was recrystallized repeatedly from ethanol to yield pure product melting at 81.8°–83.2°.

Calcd. for $C_{21}H_{32}N_2O$: C, 76.78; H, 9.82; N, 8.53. Found: C, 77.92; H, 9.09; N, 8.67.

I claim:
1. A method for inducing an antifertility effect in a male aves or mammal, which comprises orally or parenterally administering an antifertility effective amount of a compound of the formula

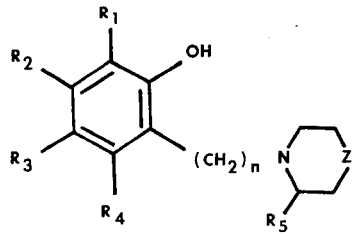

wherein
Z is —O— or —$CH_2$—, $R_1$ independently is hydrogen, N-piperidino-lower alkyl and N-α-pipecolino lower alkyl,
$R_2$, $R_3$ and $R_4$ independently are hydrogen or lower alkyl,
$R_1$, $R_2$, $R_3$ and $R_4$ taken together as adjacent pairs are lower alkyl having from 3 to 5 carbon atoms, $R_5$ is hydrogen or lower alkyl and $n$ is 1 or 2
or the enantiomer or acid addition salts thereof to said aves or mammal.

2. The method of claim 1 wherein said compound is administered orally.

3. The method of claim 1 wherein said compound is D,L-6-(N-α-pipecolinomethyl)-5-hydroxyindane.

4. The method of claim 1 wherein said compound is the maleate salt of D,L-6-(N-α-pipecolinomethyl)-5-hydroxyindane.

5. The method of claim 1 wherein said compound is an enantiomer of 6-(N-α-pipecolinomethyl)-5-hydroxyindane maleate.

6. The method of claim 1 wherein said compound is contained in an oral pharmaceutical dosage unit in an amount in the range of from about 0.5 mg. to 1,000 mg., the remainder of the composition being a conventional pharmaceutical oral carrier.

7. The method of claim 1 wherein said compound is contained in a conventional pest bait composition in the range of from about 0.05 wt/% to about 1.0 wt/%.

8. A method for inducing temporary sterility in a male mammal which comprises orally administering a compound of the formula

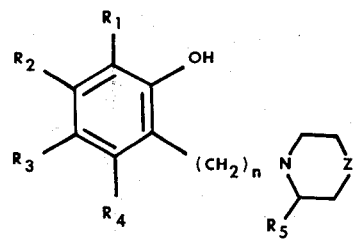

wherein
Z is —O— or —$CH_2$—, $R_1$ independently is hydrogen, N-piperidino-lower alkyl and N-α-pipecolino lower alkyl,
$R_2$, $R_3$ and $R_4$ independently are hydrogen or lower alkyl,
$R_1$, $R_2$, $R_3$ and $R_4$ taken together as adjacent pairs are lower alkyl having from 3 to 5 carbon atoms, $R_5$ is hydrogen or lower alkyl and $n$ is 1 or 2
or the enantiomer or acid addition salts thereof to said male mammal in a dosage in the range of from about 0.4 mg/kg/day to about 75 mg/kg/day.

* * * * *